(12) United States Patent
Angel et al.

(10) Patent No.: US 8,809,307 B2
(45) Date of Patent: Aug. 19, 2014

(54) PHARMACEUTICAL FORMULATIONS CONTAINING CORTICOSTEROIDS FOR TOPICAL ADMINISTRATION

(75) Inventors: Arturo Angel, Santa Rosa, CA (US); Gordon Dow, Santa Rosa, CA (US)

(73) Assignee: Dow Pharmaceutical Sciences, Inc., Petaluma, CA (US)

( * ) Notice: Subject to any disclaimer, the term of this patent is extended or adjusted under 35 U.S.C. 154(b) by 0 days.

(21) Appl. No.: 13/287,176

(22) Filed: Nov. 2, 2011

(65) Prior Publication Data

US 2012/0129824 A1 May 24, 2012

Related U.S. Application Data

(60) Provisional application No. 61/458,339, filed on Nov. 22, 2010.

(51) Int. Cl.
*A61K 31/56* (2006.01)
*A01N 45/00* (2006.01)

(52) U.S. Cl.
USPC .......................................... 514/169; 514/180

(58) Field of Classification Search
None
See application file for complete search history.

(56) References Cited

U.S. PATENT DOCUMENTS

| 4,370,322 A | 1/1983 | Busse |
| 5,326,566 A | 7/1994 | Parab |
| 5,422,361 A * | 6/1995 | Munayyer et al. ............ 514/408 |
| 6,656,928 B1 * | 12/2003 | McCadden .................. 514/167 |
| 7,300,669 B2 | 11/2007 | Dow |
| 2005/0101582 A1 | 5/2005 | Lyons |
| 2006/0018937 A1 | 1/2006 | Friedman et al. |
| 2007/0196459 A1 | 8/2007 | Zhang |
| 2008/0044444 A1 | 2/2008 | Tamarkin |
| 2009/0012051 A1 | 1/2009 | Sugishita |
| 2010/0130460 A1 | 5/2010 | Albano |

FOREIGN PATENT DOCUMENTS

| EP | 0 513 832 A1 | 11/1992 |
| EP | 0 097 374 A2 | 1/1994 |
| NZ | 208596 | 6/1984 |
| WO | 00/24401 A1 | 5/2000 |
| WO | 01/00139 A1 | 1/2001 |
| WO | 2009/047788 | 4/2009 |
| WO | 2010/039251 | 4/2010 |

OTHER PUBLICATIONS

Smith. Podiatric Dermatology: A review of topical corticosteroids. Podiatry Management, Mar. 2006.*
Laws et al. Topical treatment of psoriasis. Expert Opin. Pharmacother. 2010. 11(12): 1999-2009.*
Barry, BW, "Vasoconstrictor activities of some novel synthetic steroids in alcoholic solution," J. Investigative Dermatology, 64(6):418-422 (1975).
"Formulation Strategies for Modulating Skin Permeation," Adrian F. Davis et al. In: Anonymous: "Dermatological and Transdermal Formulations," 2007, Informa Healthcase, USA, pp. 271-274.

* cited by examiner

*Primary Examiner* — Anna Pagonakis
(74) *Attorney, Agent, or Firm* — Kilpatrick Townsend & Stockton LLP

(57) ABSTRACT

The potency of a topical corticosteroid in a pharmaceutical formulation is maintained even when the concentration of the corticosteroid is substantially reduced by providing the corticosteroid in a formulation containing a liquid oil component that includes a dicarboxylic acid ester and/or a monocarboxylic acid ester.

28 Claims, No Drawings

PHARMACEUTICAL FORMULATIONS CONTAINING CORTICOSTEROIDS FOR TOPICAL ADMINISTRATION

This application claims priority from U.S. Provisional Patent Application Ser. No. 61/458,339, filed on Nov. 22, 2010.

BACKGROUND OF THE INVENTION

Topical corticosteroids are used to treat many acute and chronic dermatologic and mucosal disorders, especially those in which pruritus or inflammation is present. Many such conditions, such as eczema, psoriasis, and chronic dermatitis, such as hand dermatitis, are chronic conditions that require long-term therapy.

Corticosteroids for topical application are grouped within a classification system into seven classes based on potency. Topical potency of a corticosteroid is determined by a standard test, referred to as a VasoConstrictor Assay (VCA). The VCA test is described in Dow et al, U.S. Pat. No. 7,300,669, incorporated herein by reference.

Table 1 shows the classification of topical corticosteroids based on potency as determined by the VCA test.

TABLE 1

Potency Chart of Topical Corticosteroids

Class 1-Superpotent
  Clobetasol propionate 0.05%
  Betamethasone dipropionate ointment 0.05%
  Halobetasol propionate 0.05%
  Fluocinonide 0.1%
  Diflorasone diacetate ointment 0.05% (Psorcon ®)
Class 2-Potent
  Betamethasone dipropionate cream 0.05%
  Mometasone furoate ointment 0.1%
  Diflorasone diacetate cream 0.05% (Psorcon ®)
  Diflorasone diacetate ointment 0.05% (Florone ®)
  Halcinonide 0.1%
  Desoximetasone cream/ointment 0.25%
  Desoximetasone gel 0.05%
  Fluocinonide cream/gel/ointment 0.05% (Lidex ®)
  Ameinonide 0.1%
  Budesonide 0.025%
  Beclomethasone 0.025%
Class 3-Upper Mid-strength
  Fluticasone propionate ointment 0.005%
  Fluocinonide cream 0.05% (Lidex-E ®)
  Betamethasone valerate 0.12%
  Desoximetasone cream 0.05%
Class 4-Mid-strength
  Flurandrenolide ointment 0.05%
  Mometasone furoate cream 0.1%
  Triamcinolone acetonide 0.1%
  Fluocinolone acetonide 0.03%
  Hydrocortisone valerate 0.2%
Class 5-Lower Mid-strength
  Fluocinolone acetonide shampoo 0.01%
  Flurandrenolide cream/lotion/tape 0.05%
  Fluticasone propionate cream/lotion 0.05%
  Prednicarbate cream 0.1%
  Desonide lotion 0.05%
  Hydrocortisone butyrate cream/lotion/ointment/solution 0.1% (Locoid ®)
  Hydrocortisone probutate cream 0.1% (Pandel ®)
  Fluocinolone acetonide cream 0.03%/0.01% (Synalar ®)
  Hydrocortisone valerate cream 0.2%
Class 6-Mild
  Alclometasone dipropionate 0.05%
  Fluocinolone acetonide oil 0.01%
  Desonide gel 0.05%
  Fluocinonide cream/solution 0.01%
  Desonide foam 0.05%

TABLE 1-continued

Potency Chart of Topical Corticosteroids

Class 7-Least Potent
  Hydrocortisone lotion 0.5%/1%
  Hydrocortisone cream/spray/ointment 1%
  Hydrocortisone cream lotion 1%/2.5%

The most potent group of corticosteroids, determined on the basis of the VCA, is denoted Class 1 superpotent corticosteroids. In this specification, when a concentration is indicated with a particular corticosteroid, for example as an ester, an acetonide, a free alcohol, or a diester, the corticosteroid is stated as a particular form of the corticosteroid. When no concentration is indicated with a corticosteroid, or when a concentration refers to the corticosteroid in more than one form, such as an ester, an acetonide, a free alcohol, or a diester, the corticosteroid is stated without reference to the particular form. All known preparations of clobetasol propionate and halobetasol propionate, all of which are at a concentration of 0.05% w/w, are classed as superpotent corticosteroids. Other corticosteroids classified as superpotent are certain preparations of betamethasone dipropionate at a concentration of 0.05%, diflorasone diacetate at a concentration of 0.05%, and fluocinonide at a concentration of 0.1%. The next most potent group of corticosteroids is denoted Class 2 potent corticosteroids. This group includes mometasone furoate at a concentration of 0.1%, halcinonide, diflorasone diacetate, desoximetasone, fluocinonide at a concentration of 0.05%, and cream formulations of betamethasone at a concentration of 0.05%.

The superpotent corticosteroids are utilized for skin conditions that are not satisfactorily responsive to lower potency corticosteroids. Such conditions include psoriasis and certain severe types of eczema. Unfortunately, because of the high potency of the Class 1 corticosteroids, which correlates with a high incidence and severity of systemic side effects, including hypothalamic-pituitary-adrenal (HPA) axis suppression, topical treatment with superpotent corticosteroids is generally limited in duration to 2 weeks. Such side effects may also occur with treatment with Class 2 potent corticosteroids. Additionally, the occurrence of local adverse reactions limits the duration of use of superpotent and potent corticosteroids with respect to treatment of chronic or recurrent skin diseases.

Chronic skin conditions, such as psoriasis, however often require long periods of treatment, greater than 2 weeks, to manage such conditions. Therefore, it would be desirable to have a superpotent corticosteroid formulation with a reduced incidence and/or severity of systemic side effects so that therapy can be continued for durations longer than 2 weeks.

Dow, U.S. Patent Publication 2006/0239929 discloses a spray formulation containing 0.05% clobetasol that was shown to be efficacious and to have few serious side effects when administered for periods of 4 weeks. The disclosure of Dow, however, was limited to a spray formulation and the prosecution history of this application shows that prior art formulations of 0.05% clobetasol are associated with high frequencies of serious systemic side effects, including hypothalamic-pituitary-adrenal axis suppression when applied for a period of 2 weeks.

Because of the tendency of all superpotent corticosteroids to cause serious systemic effects, the FDA (Food and Drug Administration) requires that the prescribing information for currently marketed topical compositions of superpotent corticosteroids, such as clobetasol and halobetasol, except for a particular spray formulation of clobetasol, carry the warning that treatment beyond 2 consecutive weeks is not recommended, and the total dosage should not exceed 50 g of the composition per week. Regarding the clobetasol spray formulation, the prescribing information states that treatment should be limited to 4 weeks and that treatment beyond 2 weeks should be limited to localized lesions of moderate to severe plaque psoriasis that have not sufficiently improved after two weeks. Regarding potent corticosteroids, the FDA does not require the prescribing information to carry this warning, but does caution the physician to be aware of and to monitor for the occurrence of HPA axis suppression.

Busse, U.S. Pat. No. 4,370,322, concerns the problem of systemic side effects due to topical application of high-potency corticosteroids. Busse discloses a topical pharmaceutical composition containing a high-potency corticosteroid and an oil phase that contains a low viscosity oily solvent, wherein the concentration of the liquid oil phase is at least three times that which is required to completely solubilize the corticosteroid. Busse discloses that, when the solvent-containing oil phase is present in such high concentrations relative to the corticosteroid, the systemic absorption of the corticosteroid is reduced but the local, desirable effects of the corticosteroid are maintained. Busse further disclose that this discovery permits the application of the same amount of steroid to achieve the same local anti-inflammatory effect while reducing unwanted systemic effects.

Parab, U.S. Pat. No. 5,326,566, in contrast to the disclosure of Busse which discloses that a high concentration oily phase will decrease systemic absorption of a corticosteroid when applied to the skin, discloses that, when a formulation contains a skin penetration enhancing amount of dibutyl adipate or a mixture of dibutyl adipate and isopropyl myristate at a concentration that is sufficient to dissolve the corticosteroid in the formulation but which is less than 1.5 times that which is required to dissolve the corticosteroid, the penetration of the corticosteroid through skin and into the systemic circulation is increased rather than decreased. Thus, Parab discloses that formulations containing a corticosteroid and an oily phase containing dibutyl adipate, alone or in combination with isopropyl myristate, at a concentration between 1 and 1.5 times that required to dissolve the corticosteroid are useful for increasing the systemic absorption of a topically applied corticosteroid.

DESCRIPTION OF THE INVENTION

It has been unexpectedly discovered that the potency of a topical corticosteroid, including superpotent and potent topical corticosteroid as determined by VCA test described above, is maintained even when the concentration of the corticosteroid is substantially reduced by providing the corticosteroid in a formulation containing a liquid oil component that includes a dicarboxylic acid ester and/or a monocarboxylic acid ester. Because the potency of the corticosteroid is maintained, even when the concentration of the corticosteroid is markedly reduced, the desired dermatological effects of the treatment are obtained. Due to the much reduced concentration of the corticosteroid in the formulation, reduced amounts of corticosteroid are available to enter the systemic circulation and, therefore, the tendency of such formulations to cause undesirable systemic side effects should likewise be reduced. Thus, the formulations and methods of this application are especially useful for the treatment of chronic or recalcitrant skin diseases, such as psoriasis, due to the concerns regarding safety when topical corticosteroids are used in multiple course treatments over time.

Accordingly, one embodiment of the invention is a pharmaceutical formulation for topical administration to the skin which contains a corticosteroid at a concentration below that which is presently utilized in topical formulations and which provides substantially an equivalent potency to formulations having the higher concentrations that are presently utilized. Thus, for superpotent corticosteroids other than fluocinonide, such as halobetasol propionate and clobetasol propionate, the formulation contains the corticosteroid at a concentration less than 0.05% w/w and for fluocinonide the formulation contains the corticosteroid at a concentration less than 0.05% w/w. Similarly, for potent corticosteroids other than mometasone, halcinonide, and beclomethasone, the formulation contains the corticosteroid at a concentration less than 0.05%, and in the case of mometasone or halcinonide, less than 0.1%, and in the case of beclomethasone, less than 0.025%.

The liquid oil component of the present application includes all ingredients of the formulation that are practically insoluble or insoluble in water and which are liquid at room temperature of 22° C. Other than the dicarboxylic acid ester and monocarboxylic acid esters discussed herein, the liquid oil component may contain additional components such as hydrocarbons like mineral oil, light mineral oil, squalene, and squalane, fatty alcohols such as octylododecanol and isostearyl alcohol, fatty acids such as isostearic acid and oleic acid, and triglycerides such as peanut oil, and fractionated coconut oil.

In addition to the liquid oil component, the formulation may contain water insoluble or practically insoluble ingredients that are not liquid at room temperature. However, as discussed in further detail below, it is the liquid oil component of the formulation that is of importance in relation to the reduced concentration of the corticosteroid in the formulation.

The liquid oil component containing the dicarboxylic acid ester and/or the monocarboxylic acid ester in the formulation is in association with the corticosteroid in the formulation, such that the liquid oil component and the corticosteroid may interact in the formulation in order to dissolve or substantially dissolve the corticosteroid. It is hypothesized that it is this solubilization within the formulation that, upon application of the formulation to the skin of a patient, provides delivery of the corticosteroid preferentially into the skin rather than providing transdermal delivery through the skin and into the systemic circulation. As used herein, the term "substantially dissolve" means that the liquid oil component of a formulation of this invention can dissolve 25% or more of the corticosteroid in the formulation at a room temperature of 22° C.

The corticosteroid that is included in the formulation of the invention is preferably a superpotent corticosteroid according to the VasoConstrictor Assay (VCA), such as clobetasol, halobetasol, betamethasone dipropionate in augmented formulations, diflorasone diacetate in augmented formulations, and fluocinonide at 0.1%, or a potent corticosteroid, such as betamethasone dipropionate, mometasone furoate, diflorasone diacetate, halcinonide, fluocinonide, and desoximetasone.

Other steroids that are suitable for the formulation of the invention include corticosteroids other than superpotent or potent corticosteroids. Any corticosteroid that is suitable for topical application to the skin or mucous membrane of a human may be the corticosteroid of the formulation. The benefits of increased efficacy at lower concentration include reduced systemic exposure to the corticosteroid, increased local as well as systemic safety, and reduced cost of materials for making the therapeutic corticosteroid formulation. These benefits are applicable to corticosteroids of any potency, such as a corticosteroid of potency classes 3 to 7, upper mid-strength to least potent. For example desonide gel or foam is a class 6 mild corticosteroid and desonide lotion is a class 5 lower mid-strength corticosteroid. Desonide is widely used in children at a concentration of 0.05%. It is conceived that a formulation containing a concentration of desonide of less than 0.05% in which the potency is similar to that of formulations containing 0.05% desonide would be especially useful in order to reduce the total amount of steroid exposure experienced by children treated with desonide. Thus, included within the present invention are formulations containing concentrations of particular corticosteroids below those shown in Table 1. For example, the invention pertains to concentrations less than 0.005% for fluticasone propionate, concentrations less than 0.01% for fluocinolone acetonide, concentrations less than 0.025% for budesonide, beclomethasone, and triamcinolone acetonide, concentrations less than 0.05% for flurandernolide, desonide, and aclometasone dipropionate, concentrations less than 0.1% for amcinonide, betamethasone valerate, prednicarbate, hydrocortisone butyrate, and hydrocortisone probutate, and concentrations less than 0.2% for hydrocortisone valerate. The invention may also be practiced with any form of a corticosteroid, such as an ester, diester, free alcohol, or acetonide form of a corticosteroid.

The dicarboxylic acid ester (DCAE) that is suitable for the present invention has the formula $R_1OOC-(CH_2)n-COOR_2$, where $R_1$ and $R_2$ are alkyl groups containing between 1 and 4 carbons or aryl groups and may be the same or may be different and where n is straight or branched and is between 1 and 12. Examples of DCAEs containing one or more aryl groups are dibenzyl esters of dicarboxylic acids. A preferred dicarboxylic acid ester is diethyl sebacate, which has the formula $CH_3CH_2OOC-(CH_2)_8-COOCH_2CH_3$. Diethyl sebacate is considered to be typical of the dicarboxylic acid esters disclosed as each of the parameters $R_1$, $R_2$, and n of diethyl sebacate are approximately in the center of the range of each of the specified parameters.

Examples of other suitable dicarboxylic acid esters where $R_1=R_2$ are dimethyl, diethyl, dipropyl, diisopropyl, dibutyl and diisobutyl esters such as oxalate, malate, succinate, glutarate, adipate, pimelate, suberate, and azalate. Examples of suitable dicarboxylic acid esters where $R_1 \neq R_2$ are methyl ethyl, methyl propyl, methyl butyl, methyl isopropyl, ethyl propyl, ethyl butyl, ethyl isopropyl, and propyl butyl esters such as oxalate, malate, succinate, glutarate, adipate, pimelate, suberate, azalate, and sebacate.

Alternatively, or in combination with the DCAE, the formulation may contain a monocarboxylic acid ester (MCAE). The MCAE that is suitable for the present invention has the formula $CH_3-(CH_2)_n-COOR_1$, where $R_1$ is an alkyl group containing between 1 and 4 carbons or an aryl group, and where n is straight or branched and is between 1 and 12. Examples of such monocarboxylic acid esters include methyl, ethyl, propyl, isopropyl, butyl, or an aryl such as benzyl formate, acetate, propionate, butyrate, valerate, laurate, myristate, palmitate, and stearate. Examples of preferred monocarboxylic acid esters are isopropyl palmitate and isopropyl myristate.

The corticosteroid composition of the present invention may be any formulation that incorporates DCAE and/or MCAE such as ointments, solutions, gels, foams and emulsions including creams and lotions. Preferably, the formulation is an emulsion in which an internal oil component is dispersed within an external aqueous phase or an internal aqueous phase is dispersed within an external oil component. Examples of emulsions include water-in-oil, oil-in-water, water-in-oil-in-water emulsion, and oil-in-water-in-oil emulsions. The emulsion may be a macroemulsion, a microemulsion, or a nanoemulsion. Also contemplated are other formulations in which an oil phase and a water phase coexist within the formulation, such as a multivesicular emulsion, which is not a true emulsion, disclosed in Espinoza, U.S. Pat. No. 6,709,663. Also contemplated is a liposomal dispersion in which, preferably, the DCAE is incorporated in the lipid component of the liposomes. Also contemplated are other formulations in which non-polar and polar liquid ingredients coexist with the formulation.

Preferably, the formulation of the invention contains a thickening agent to provide viscosity so that the formulation may be provided in the form of a lotion, gel, cream, or ointment. Preferably but not necessarily, the thickening agent is miscible or soluble in an aqueous fluid. Examples of suitable thickening agents include acacia, alginic acid, bentonite, carbomers, also known as carboxy vinyl polymers, such as sold under the tradename Carbopol® (Lubrizol, Wickliffe, Ohio), carboxymethylcellulose, ethylcellulose, gelatin, hydroxyethylcellulose, hydroxypropyl cellulose, magnesium aluminum silicate, methylcellulose, poloxamers, polyvinyl alcohol, sodium alginate, tragacanth, and xanthan gum. The thickening agent may also reside in the oil or lipophilic portion of the formulation. Examples of suitable lipophilic thickening agents include cetyl alcohol, stearyl alcohol, glyceryl stearate, white beeswax, microcrystalline wax, hydrogenated polyisobutane polymers, and emulsifying wax.

If desired or required in order to obtain the form of the formulation desired, a surfactant or emulsifier may be included. The emulsifier is preferably a non-ionic emulsifier such as a sorbitan ester, a polyoxyethylene derivative of a sorbitan ester or a glyceryl ester; a polymeric emulsifier such as a acrylates/C10-C30 alkyl acrylate crosspolymer such as those sold under the tradename PEMULEN® (The Lubrizol Corporation, Wickliffe, Ohio); or an anionic emulsifier such as an alkali soap such as sodium or potassium oleate, an amine soap such as triethanolamine stearate, a detergent such as sodium lauryl sulfate, sodium dioctyl sulfosuccinate, and sodium docusate. Less preferred are cationic emulsifiers such as quaternary ammonium salts. Particular examples of suitable anionic and non-ionic emulsifiers include glyceryl monostearate, polyoxyethylene monooleate, polyoxyethylene monostearate, polyoxyethylene monolaurate, potassium oleate, sodium lauryl sulfate, sodium oleate, sorbitan monolaurate, sorbitan monopalmitate, sorbitan monostearate, sorbitan tristearate, sorbitan monooleate, sorbitan trioleate, triethanolamine oleate, polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, and polyoxyethylene sorbitan trioleate.

The formulation may contain other pharmaceutically acceptable excipients. Preferably, the formulation contains a humectant such as glycerin, sorbitol, hexylene glycol, urea, or propylene glycol. Preferably, the formulation contains an emollient such as petrolatum, lanolin, mineral oil, light mineral oil, stearic acid, cyclomethicone, or dimethicone. Additional optional excipients include stabilizers, preservatives such as methylparaben, pHH adjusting agents such as sodium hydroxide, chelating agents such as EDTA and its salts, and buffers.

The formulation may include other lipophilic liquids in an amount that is sufficient to be miscible with the dicarboxylic acid ester and/or monocarboxylic acid ester. The lipophilic liquid may be an emollient such as lanolin oil, mineral oil, light mineral oil, isostearic acid, squalene, octyldodecanol, fractionated coconut oil, cyclomethicone, or dimethicone.

The formulation of the invention may be made by any method known to make a uniphase or multiphase pharmaceutical formulation for topical administration. In order to make a multiphase formulation such as an emulsion, for example, the components of the aqueous phase and of the oil phase may be separately combined and mixed until homogenous solutions are obtained and then the aqueous solution and the oil solution may be combined and mixed, such as by shear mixing, to form the formulation. The oil phase may be added to the water phase, or the water phase may be added to the oil phase. The phases may be combined and mixed, such as at elevated temperatures of 50-90° C. or at room temperature, that is between 20-30° C., or at a temperature between room temperature and the elevated temperatures.

The formulation may be used for topical treatment or prophylaxis of a dermatological or mucosal disorder that is responsive to the application of topical corticosteroids. Examples of such disorders include psoriasis, dermatitis such as atopic, contact, or hand dermatitis, eczema, and poison ivy dermatitis.

The concentration of the corticosteroid in the formulation is that which is sufficient to provide an anti-inflammatory response to an area of skin or mucous membrane to which it is applied. The concentration may vary depending on the particular disorder to be treated, the particular corticosteroid utilized, and other parameters.

Because the primary purpose to which the invention is conceived to pertain is to reduce the amount of corticosteroid that is available to enter the systemic circulation following the topical administration of corticosteroids, the preferred concentration of corticosteroid in the formulation of the invention is less than that present in prior art topical formulations containing the same corticosteroid. For example, both clobetasol propionate and halobetasol propionate topical formulations are presently available as creams and ointments in a concentration of 0.05% w/w. Thus, it is preferred that the concentration of such corticosteroid in the formulation of the present invention is less than 0.05% w/w. However, concentrations of corticosteroid at the same level, that is at 0.05%, or higher, are not excluded from the scope of the present invention unless indicated as such in the claims.

In a preferred embodiment, the formulation of the invention contains a concentration of the corticosteroid such as clobetasol propionate or halobetasol propionate that is 80% or less than that presently available, that is a concentration of 0.04% or less. In another preferred embodiment, the formulation contains a concentration of the corticosteroid that is 60% or less than that presently available, that is a concentration of 0.03% or less. In another preferred embodiment, the concentration is 50% or less than that presently available, that is a concentration is 0.025% or less. In another preferred embodiment, the formulation of the invention contains a concentration of corticosteroid that is 40% or less than that presently available, that is has a concentration of 0.02% or less. In another preferred embodiment, the formulation contains a concentration of the corticosteroid that is 20% or less than that presently available, that is has a concentration of 0.01% or less. In another preferred embodiment, the concentration of corticosteroid in the formulation of the invention is 10% or less than that presently available, that is 0.005% or less.

The concentration of the liquid oil component of the formulation containing a DCAE and/or an MCAE is at least that which is sufficient to dissolve at least 25% of the entire amount of the corticosteroid in the formulation at a room temperature of 22° C. In one embodiment, the concentration of the liquid oil component is sufficient to dissolve between 25% and 50% of the corticosteroid, such as about 40%. In a preferred embodiment, the concentration of the liquid oil component is sufficient to dissolve between 50% and 60% of the corticosteroid, such as about 55%. In another preferred embodiment, the concentration of the liquid oil component is sufficient to dissolve between 60% and 70% of the corticosteroid, such as about 65%. In another preferred embodiment, the concentration of the liquid oil component is sufficient to dissolve between 70% and 80% of the corticosteroid, such as about 75%. In another preferred embodiment, the concentration of the liquid oil component is sufficient to dissolve between 80% and 90% of the corticosteroid, such as about 85%. In another preferred embodiment, the concentration of the liquid oil component is sufficient to dissolve between 90% and 100% of the corticosteroid, such as about 95%.

In a more preferred embodiment, the concentration of the liquid oil component is sufficient to dissolve 100% or more of the corticosteroid in the formulation at a room temperature of 22° C. For example the concentration of the liquid oil component may be between 1.0 and 1.5 times that which is sufficient to dissolve the entire amount of the corticosteroid in the formulation. For example, the concentration of the liquid oil component may be greater than 1.5 times that which is sufficient to dissolve the entire amount of the corticosteroid in the formulation, such as between 1.5 times and 3.0 times that which is sufficient to dissolve the amount of corticosteroid in the formulation. For example, the concentration of the liquid oil component may be more than 3.0 times that which is sufficient to dissolve the entire amount of the corticosteroid in the formulation. Examples of suitable concentrations of liquid oil component in terms of amount required to dissolve the entire amount of corticosteroid in the formulation at room temperature include 0.25, 0.4, 0.5, 0.75, 1.0, 1.05, 1.15, 1.25, 1.25, 1.24, 1.45, 2.0, 2.5, 3.0, 3.5, 4.0, 4.5, 5.0, 5.5, and 6.0 times or higher than that which is sufficient to dissolve the corticosteroid in the formulation at a room temperature of 22° C.

The combined concentrations of the DCAE and/or the MCAE in the liquid oil component of the formulation is at least about 10% of the oil component, such as at least 20%, 30%, 40%, 50%, 60%, 70%, 80%, or 90% of the oil component. In one preferred embodiment, the DCAE, and MCAE if present, constitute 100% of the liquid oil component of the formulation.

The formulation of the invention maintains a VCA score as high or that is similar to the VCA score that is obtained by the application of prior art formulations containing higher concentrations of the corticosteroid, such as the superpotent corticosteroid. Because the VCA score is determinative of local efficacy, the formulation of the invention, even at greatly reduced concentrations of corticosteroid, would be understood by one of skill in the art to be generally as effective locally in the skin as presently available formulations containing higher concentrations of corticosteroid. Additionally, because of the reduced concentration of corticosteroid in the formulation compared to that in the prior art compositions and the concomitant reduction in amount of corticosteroid that is available to enter the systemic circulation upon topical administration of the formulation, it is conceived that the formulation may have similar efficacy but improved safety compared to prior art formulations that contain higher concentrations of corticosteroid. Thus the formulations of this application have particular utility in infants and children in treating skin diseases such as atopic dermatitis and in both adults and children for treating recalcitrant or chronic skin diseases such as psoriasis. It is conceived that the present invention provides an equivalent or better efficacy in treating steroid responsive skin diseases compared to that produced by presently available topical formulations, and with potentially reduced local and systemic side effects.

The invention is further illustrated in the following non-limiting examples. In the examples, halobetasol propionate is utilized as an exemplary superpotent corticosteroid and diethyl sebacate is utilized as an exemplary dicarboxylic acid ester. It is understood, however, that halobetasol propionate is illustrative of the superpotent and potent corticosteroids, that diethyl sebacate is illustrative of the DCAE, and that isopropyl myristate is illustrative of the MCAE, and that any corticosteroid, especially potent or superpotent corticosteroid, DCAE, or MCAE may be substituted for the illustrated halobetasol propionate, diethyl sebacate, and/or isopropyl myristate with similar results.

EXAMPLE 1

Formulations

The following formulations as shown in Table 1 were made containing the superpotent corticosteroid halobetasol as halobetasol propionate (HP). Formulations A to D are formulations of the invention. Formulation E is a formulation that is not within the scope of the present invention.

TABLE 1

| Ingredients | Formulation A | B | C | D | E |
|---|---|---|---|---|---|
| | % w/w | | | | |
| Halobetasol Propionate (corticosteroid) | 0.035 | 0.025 | 0.01 | 0.035 | 0.035 |
| Diethyl Sebacate (DCAE) | 3.0 | 2.1 | 0.8 | 0.9 | |
| Isopropyl Myristate (MCAE) | | | | | 11.0 |
| Light Mineral Oil | 1.0 | 0.7 | 0.3 | | |
| Medium Chain Triglycerides | | | | | 18.0 |
| White Petrolatum | | | | | 2.0 |
| Butylated Hydroxytoluene | | | | | 0.01 |
| Sorbitan Monooleate | 0.1 | 0.1 | 0.1 | 0.1 | |
| Cholesterol | | | | | 0.5 |
| Stearyl Alcohol | | | | | 1.0 |
| Cetyl Alcohol | | | | | 0.5 |
| Propylene Glycol | 7.5 | 7.5 | 7.5 | 7.5 | 7.5 |
| Disodium Edetate Dihydrate | 0.05 | 0.05 | 0.05 | 0.05 | 0.05 |
| Pemulen ® TR-1 | 0.40 | 0.40 | 0.40 | 0.40 | 0.40 |
| Carbopol ® 981 | 0.60 | 0.60 | 0.60 | 0.60 | 0.60 |
| Methylparaben | 0.17 | 0.17 | 0.17 | 0.17 | 0.17 |
| Propylparaben | 0.03 | 0.03 | 0.03 | 0.03 | 0.03 |
| Sodium Hydroxide | q.s. pH 6.0 +/− 1 | | | | |
| Purified Water | q.s.ad 100 | | | | |

EXAMPLE 2

Determination of Saturation Solubility and Degree of Saturation

The saturation solubility of halobetasol propionate in each of formulations A to D of Example 1 was determined as follows. At a temperatures of 22°+/−2° C., samples containing halobetasol in the liquid oil component components of formulations A to D, respectively, were prepared and stored in glass vials. The samples were shaken at 395 to 405 oscillations/minute for approximately 72 hours using a Burrell WRIST-ACTION® Shaker Model 75 (Burrell Scientific, Pittsburgh, Pa.). Samples were then centrifuged for 40 minutes at 3500 rpm and the supernatant was collected. The supernatant was filtered using 0.45 μm PTFE ACRODISC® Pall syringe filter (Pall Corporation, Port Washington, N.Y.). The filtered samples were analyzed by HPLC using a reverse phase column monitored at 254 nm UV detection. The degree of unsaturation of halobetasol propionate of each formulation was then calculated by multiplying the concentration (% w/w) of the liquid oil component by the saturation solubility of halobetasol in the liquid oil component components and dividing by the concentration of halobetasol propionate in the formulation. The data is shown below in Table 2.

TABLE 2

| Formulation | Concentration of Liquid Oil component (% w/w) | Saturation Solubility (w/w) % | Degree of Unsaturation |
|---|---|---|---|
| A | 4 | 2.41 | 2.8 |
| B | 2.8 | 2.41 | 2.7 |
| C | 1.1 | 2.41 | 2.5 |
| D | 11.9 | 0.45 | 1.5 |

EXAMPLE 3

Determination of VCA Scores

The mean VCA score of each of the formulations of Example 1 was determined as described in Dow, U.S. Pat. No. 7,300,669 and was assigned a semi-quantitative subjective evaluation score on a scale of 0 to 4. The mean VCA score of a formulation corresponding to that of the commercial product Ultravate® 0.05%; NDC 0072-1400-50 (Bristol-Meyers Squibb Company, Princeton, N.J.) was also determined. In contrast to the other formulations tested, Ultravate contains halobetasol propionate at a concentration of 0.05%. In determining the mean VCA score, the evaluator was blinded as to the formulation being tested. The results are shown in Table 3.

TABLE 3

| Formulation | HP Conc (% w/w) | VCA Mean Score |
|---|---|---|
| A | 0.035 | 2.37 |
| B | 0.025 | 2.40 |
| C | 0.010 | 2.47 |
| D | 0.035 | 2.43 |
| E | 0.035 | 1.77 |
| Ultravate ® | 0.050 | 2.37 |

As shown in Table 3, each of the formulations A to D of the present invention provided a VCA score similar to that of the prior art formulation Ultravate®. This high level of VCA score, which is indicative of the local desired response of the corticosteroid, was obtained even though the level of corticosteroid in the formulations of the invention are markedly lower than that in the prior art formulation. Formulation E, which contained the same concentration of corticosteroid as in Formulations A and D, had a markedly lower VCA score.

EXAMPLE 4

Lotion Formulations

Lotion formulations 4a and 4b of the present invention contain the ingredients shown in Table 4. These formulations may be made as follows.

A separate aqueous phase is made. In a manufacturing vessel, purified water and disodium edetate dihydrate are combined and the mixture is agitated until a clear solution is achieved. Sorbitol, methylparaben, and propylparaben are then added to the mixture. The mixture is continuously mixed and is heated to approximately 75° C. The mixture is agitated until a solution is obtained. The mixture is then removed from the heat source and allowed to cool to below 40° C. with continued mixing. With continuous propeller agitation Carbopol 981 and Pemulen TR-1 are added to the mixture and dispersed. The propeller mixing is continued until the polymers are fully dispersed and hydrated.

A separate oil phase is made. In a vessel diethyl sebacate and halobetasol propionate are combined. The mixture is agitated until a solution is achieved. With continuous propeller mixing, light mineral oil and sorbitan monooleate are added. Mixing is continued until a solution is obtained.

In a separate vessel, a 1N solution of sodium hydroxide is prepared.

With high speed rotor-stator mixing, the oil phase containing the drug (halobetasol propionate) is, added to the aqueous phase. Mixing is continued until a homogeneous emulsion is obtained. Propeller mixing is then used in place of the high speed rotor-stator mixing. With continuous mixing an appropriate amount of the sodium hydroxide solution is added incrementally to obtain a pH of 5.5±0.5. Propeller mixing is continued until a homogeneous lotion is obtained.

TABLE 4

| | % w/w | |
|---|---|---|
| Ingredients | Formula 4A | Formula 4B |
| Halobetasol Propionate | 0.01 | 0.025 |
| Diethyl Sebacate | 2.97 | 2.90 |
| Light Mineral Oil | 8.03 | 2.90 |
| Sorbitan Monooleate | 0.10 | 0.10 |
| Sorbitol Solution, 70% | 10.7 | 10.7 |
| Disodium Edetate, Dihydrate | 0.05 | 0.05 |
| Pemulen TR-1 | 0.40 | 0.40 |
| Carbopol 981 | 0.60 | 0.60 |
| Methylparaben | 0.17 | 0.17 |
| Propylparaben | 0.03 | 0.03 |
| Sodium Hydroxide, q. s. | pH 4.0-6.0 | pH 4.0-6.0 |
| Purified Water, q.s. ad | 100 | 100 |

EXAMPLE 5

Stability Data

A lotion formulation was made by the method of Example 4 using the ingredients listed in Table 5.

TABLE 5

| Ingredients | Percent w/w |
|---|---|
| Halobetasol propionate (HP) | 0.025 |
| Diethyl Sebacate | 2.10 |
| Light Mineral Oil | 0.70 |
| Sorbitan Monooleate | 0.10 |
| Propylene Glycol | 7.50 |
| Methylparaben | 0.17 |
| Propylparaben | 0.03 |
| Edetate Disodium, Dihydrate | 0.05 |
| Pemulen TR-1 | 0.40 |
| Carbopol 981 | 0.60 |
| Sodium Hydroxide | q.s. ad pH 5.0 |
| Purified Water | q.s. ad 100 |

The formulation was packaged in glass screw-cap jars and tested for stability at refrigerator temperature (5° C.), room temperature (25° C.), and accelerated temperature (40° C.) and tested at the beginning of the study and periodically for up to 6 months. Description was performed by visual observation, pH was measured with a calibrated pH meter, and viscosity was measured with a Brookfield rotational viscometer using spindle 27 and a speed of 12 rpm. The content of halobetasol propionate was determined by reverse phase HPLC using a C18 column and UV detection. The stability specifications for the halobetasol lotion that would be required for a commercial product would typically be as shown in Table 6.

TABLE 6

| PARAMETER | FDA REQUIREMENT |
|---|---|
| Description | no substantial change |
| pH | 4.0 to 6.0 |
| Viscosity | 7,500 to 15,000 cps |
| HP Content | 90 to 110% of labeled amount |

The physical and chemical stability test results for this formulation are indicated below in Table 7.

TABLE 7

| Condition | Time | Description | pH | Viscosity (cps) | HP Content (% of labeled amount) |
|---|---|---|---|---|---|
| Initial | 0 months | White to off-White Lotion | 5.1 | 10,833 | 99.4 |
| 5° C. | 6 months | Conforms | 5.1 | 12,285 | 94.0 |
| 25° C. | 3 months | | 5.1 | 12,140 | 95.3 |
| | 6 months | | 5.1 | 13,215 | 92.1 |
| 40° C. | 1 months | | 5.1 | 12,090 | 95.1 |
| | 3 months | | 5.1 | 12,090 | 93.4 |
| | 6 months | | 5.1 | 12,070 | 92.5 |

The HP lotion was determined to be within the typical specifications at all test times. The data of Table 6 indicates that this lotion product would be expected to have a 2 year shelf life at room temperature based on the favorable results after 6 months at 40° C.—the accelerated condition accepted by the Food and Drug Administration to support a 2 year product shelf life at room temperature.

Further modifications, uses, and applications of the invention described herein will be apparent to those skilled in the art. It is intended that such modifications be encompassed in the following claims.

The invention claimed is:

1. A pharmaceutical composition for topical application to the skin of an individual comprising halobetasol propionate at a concentration of 0.04% or less and a liquid oil component comprising one or more dicarboxylic acid esters, wherein the dicarboxylic acid esters are selected from diethyl sebacate, diisopropyl adipate, and dibutyl sebacate and wherein at least 25% of the halobetasol propionate is solubilized in the liquid oil component at 22° C.

2. The pharmaceutical composition of claim 1 wherein the concentration of the halobetasol propionate is 0.025% or less.

3. The pharmaceutical composition of claim 2 wherein the concentration of the halobetasol propionate is 0.01% or less.

4. The pharmaceutical composition of claim 1 wherein the concentration of the liquid oil component is sufficient to dissolve the amount of halobetasol propionate in the composition at a temperature of 22° C.±2° C.

5. The pharmaceutical composition of claim 4 wherein the concentration of the liquid oil component is between 1.5 and 3 tunes that required to completely solubilize the amount of halobetasol propionate in the composition at a temperature of 22° C.±2° C.

6. The pharmaceutical composition of claim 5 wherein the concentration of the liquid oil component is between 1.75 and 2.75 times that required to completely solubilize the amount of halobetasol propionate in the composition at a temperature of 22° C.±2° C.

7. The pharmaceutical composition of claim 1 wherein the concentration of the esters in the liquid oil component is at least 30% of the concentration of the liquid oil component in the composition.

8. The pharmaceutical composition of claim 7 wherein the concentration of the esters in the liquid oil component is at least 50% of the concentration of the liquid oil component in the composition.

9. The pharmaceutical composition of claim 8 wherein the concentration of the esters in the liquid oil component is at least 70% of the concentration of the liquid oil component in the composition.

10. The pharmaceutical composition of claim 9 wherein the concentration of the esters in the liquid oil component is at least 90% of the concentration of the liquid oil component in the composition.

11. The pharmaceutical composition of claim 10 wherein the concentration of the esters in the liquid oil component is 100% of the concentration of the liquid oil component in the composition.

12. The pharmaceutical composition of claim 1 wherein the dicarboxylic acid ester is diethyl sebacate.

13. The pharmaceutical formulation of claim 1 wherein the halobetasol propionate is at a concentration of 0.025% or less, the liquid oil component comprises diethyl sebacate, and wherein at least 50% of the halobetasol propionate is solubilized in the liquid oil component at room temperature.

14. The pharmaceutical formulation of claim 13 wherein the concentration of the liquid oil component is between 1.5 and 3 times that required to completely solubilize the amount of halobetasol propionate in the composition at a temperature of 22° C.±2° C.

15. A method for treating a disorder of the skin that is amenable to treatment with a topical corticosteroid comprising providing a pharmaceutical composition of claim 1 and applying an amount to the skin that is effective in ameliorating the signs or symptoms of the disorder.

16. A method for treating a disorder of the skin that is amenable to treatment with a topical corticosteroid comprising providing a pharmaceutical composition of claim 4 and applying an amount to the skin that is effective in ameliorating the signs or symptoms of the disorder.

17. A method for treating a disorder of the skin that is amenable to treatment with a topical corticosteroid comprising providing a pharmaceutical composition of claim 13 and applying an amount to the skin that is effective in ameliorating the signs or symptoms of the disorder.

18. The pharmaceutical composition of claim wherein the concentration of the halobetasol propionate is 0.035%.

19. The pharmaceutical composition of claim 1, wherein the liquid, oil component further comprises light mineral oil.

20. The pharmaceutical composition of claim 19, wherein the liquid oil component comprises diethyl sebacate and light mineral oil.

21. The pharmaceutical composition of claim 1, wherein the liquid oil component comprises diethyl sebacate and isopropyl myristate.

22. A pharmaceutical composition for topical application to the skin of an individual comprising halobetasol propionate at a concentration of 0.04% or less and a liquid oil component comprising one or more dicarboxylic acid esters, wherein the dicarboxylic acid esters are selected from diethyl sebacate, diisopropyl adipate, and dibutyl sebacate and wherein the concentration of the liquid oil component is between 1.5 and 3 times that required to completely solubilize the amount of halobetasol propionate in the composition at a temperature of 22° C.±2° C.

23. The pharmaceutical composition of claim 22, wherein the concentration of the esters in the liquid oil component is at least 30% of the concentration of the liquid oil component in the composition.

24. The pharmaceutical composition of claim 22, wherein the concentration of the esters in the liquid oil component is at least 50% of the concentration of the liquid oil component in the composition.

25. The pharmaceutical composition of claim 22, wherein the concentration of the esters in the liquid oil component is at least 70% of the concentration of the liquid oil component in the composition.

26. The pharmaceutical composition of claim 22, wherein the concentration of the esters in the liquid oil component is at least 90% of the concentration of the liquid oil component in the composition.

27. The pharmaceutical composition of claim 22, wherein the concentration of the esters in the liquid oil component is 100% of the concentration of the liquid oil component in the composition.

28. The pharmaceutical composition of claim 22, wherein the liquid oil component further comprises light mineral oil.

* * * * *

UNITED STATES PATENT AND TRADEMARK OFFICE
CERTIFICATE OF CORRECTION

PATENT NO. : 8,809,307 B2  Page 1 of 1
APPLICATION NO. : 13/287176
DATED : August 19, 2014
INVENTOR(S) : Angel et al.

It is certified that error appears in the above-identified patent and that said Letters Patent is hereby corrected as shown below:

In the Claims:

In Column 14, line 8, Claim 18: after "of claim" please insert --1,--.

In Column 14, line 11, Claim 19: delete "liquid, oil" and please insert --liquid oil--.

Signed and Sealed this
Twenty-first Day of July, 2015

Michelle K. Lee
*Director of the United States Patent and Trademark Office*